(12) United States Patent
Liu et al.

(10) Patent No.: US 12,716,975 B2
(45) Date of Patent: Aug. 25, 2026

(54) INTERFERENCE CANCELLATION METHOD, MEDIUM, AND DEVICE

(71) Applicant: HANGZHOU WEIYING MEDICAL TECHNOLOGY CO., LTD., Zhejiang (CN)

(72) Inventors: Yilong Liu, Zhejiang (CN); Ruixing Zhu, Zhejiang (CN)

(73) Assignee: HANGZHOU WEIYING MEDICAL TECHNOLOGY CO., LTD., Zhejiang (CN)

( * ) Notice: Subject to any disclaimer, the term of this patent is extended or adjusted under 35 U.S.C. 154(b) by 502 days.

(21) Appl. No.: 18/270,599

(22) PCT Filed: Apr. 20, 2022

(86) PCT No.: PCT/CN2022/088036

§ 371 (c)(1),
(2) Date: Jun. 30, 2023

(87) PCT Pub. No.: WO2022/228253

PCT Pub. Date: Nov. 3, 2022

(65) Prior Publication Data

US 2024/0061060 A1 Feb. 22, 2024

(30) Foreign Application Priority Data

Apr. 29, 2021 (CN) ........................ 202110477311.7

(51) Int. Cl.
*G01R 33/565* (2006.01)
*A61B 5/00* (2006.01)
(Continued)

(52) U.S. Cl.
CPC .......... *G01R 33/565* (2013.01); *A61B 5/0042* (2013.01); *A61B 5/055* (2013.01);
(Continued)

(58) Field of Classification Search
CPC G01R 33/565; G01R 33/4806; G01R 33/583; A61B 5/369; A61B 5/0042; A61B 5/055
See application file for complete search history.

(56) References Cited

U.S. PATENT DOCUMENTS 5,461,314 A * 10/1995 Arakawa ............ G01R 33/3628 324/318
2010/0074365 A1* 3/2010 Ladebeck ............ G01T 1/1603 375/350

(Continued)

FOREIGN PATENT DOCUMENTS

CN 106164694 A 11/2016
CN 107110930 A 8/2017

(Continued)

OTHER PUBLICATIONS

International Search Report from corresponding PCT Application No. PCT/CN2022/088036, dated Jun. 23, 2022.

*Primary Examiner* — Sean A Frith
(74) *Attorney, Agent, or Firm* — Harness, Dickey & Pierce, P.L.C.

(57) ABSTRACT

An interference cancellation method, a medium, and a device, capable of cancelling interference signals from measurement signals received on the basis of a plurality of channels to obtain effective signals. The method comprises: collecting, from a first-type channel, measurement signals in which effective signals and a first interference signal are mixed, and collecting a second interference signal from a second-type channel; estimating the first interference signal in the measurement signals according to a coupling relationship between first calibration data and second calibration data and on the basis of the second interference signal; removing the first interference signal from the measurement signals to obtain a target effective signal; wherein the first calibration data and the second calibration data are interfer- (Continued)

ence signals respectively collected from the first-type channel and the second-type channel when an electronic device is in a preset state.

12 Claims, 5 Drawing Sheets

(51) Int. Cl.
*A61B 5/055* (2006.01)
*A61B 5/369* (2021.01)
*G01R 33/48* (2006.01)
*G01R 33/58* (2006.01)

(52) U.S. Cl.
CPC .......... *A61B 5/369* (2021.01); *G01R 33/4806* (2013.01); *G01R 33/583* (2013.01)

(56) References Cited

U.S. PATENT DOCUMENTS

2016/0038091 A1* 2/2016 Krishnaswamy .... A61B 5/1102 600/483
2016/0069970 A1* 3/2016 Rearick ............. G01R 33/3802 324/309
2016/0128592 A1* 5/2016 Rosen .................... A61B 5/389 600/411
2017/0164915 A1* 6/2017 Li ............................ G01V 5/22
2018/0024215 A1 1/2018 Zhu
2021/0153765 A1* 5/2021 Sacolick ............ G01R 33/4818

FOREIGN PATENT DOCUMENTS

CN 111386470 A 7/2020
CN 112305478 A 2/2021
CN 113176528 A 7/2021

* cited by examiner

INTERFERENCE CANCELLATION METHOD, MEDIUM, AND DEVICE

CROSS-REFERENCE TO RELATED APPLICATIONS

This application is a national phase application of PCT Application No. PCT/CN2022/088036, filed on Apr. 20, 2022, which claims the benefit and priority to Chinese Patent Application No. 202110477311.7, filed on Apr. 29, 2021. The entire disclosures of the applications identified in this paragraph are incorporated herein by references.

BACKGROUND OF THE INVENTION

1. Field of the Invention

This application relates to the field of signal processing technology, in particular to an interference cancellation method, medium, and device.

2. Description of the Related Art

With the large number of the application of electrical and electronic device, people have higher and higher requirements for the quality of signals received by electronic devices. Generally, the environment in which the electronic device is located has interference, and the operation process of the electronic device and the feeder system would also generate interference, which makes the effective signals received by the electronic device would be affected by other interference signals. That is, interference signals can cause damage to the reception of effective signals, resulting in distortion of the effective signal acquired by electronic devices or a decrease in the signal-to-noise ratio (SNR).

For example, for Magnetic Resonance Imaging (MRI) device, the collected magnetic resonance imaging signals is often affected by interference signals such as electromagnetic interference (EMI) in environment, so that there are artifacts in the magnetic resonance imaging or reduce the signal-to-noise ratio of the magnetic resonance imaging, which reduces the accuracy of the magnetic resonance imaging. In order to avoid the influence of electromagnetic interference signals on the quality of the magnetic resonance imaging, it is often necessary to apply strict electromagnetic shielding to magnetic resonance imaging device, for example, placing the MRI device in specific room, however the shielding to electromagnetic would highly limit the application scenarios of MRI.

SUMMARY OF THE INVENTION

An embodiment of this application provides an interference cancellation method, a medium, and a device, capable of cancelling an interference signal from a measurement signal received from a plurality of channels to obtain an effective signal, so as to avoid the influence of the interference signal on the effective signal.

In the first aspect of the invention, there is provided an interference cancellation method, applied to an electronic device comprising first-type and second-type channels having signal reception function, comprising: collecting, from the first-type channels, a measurement signal in which an effective signal and a first interference signal are mixed, and collecting a second interference signal from the second-type channels; estimating the first interference signal in the measurement signals according to a coupling relationship between a first calibration data and a second calibration data and based on the second interference signal; removing the first interference signal from the measurement signal to obtain a target effective signal; wherein the first calibration data and the second calibration data are interference signals collected from the first-type channel and the second-type channel respectively when an electronic device is in a preset state. As an example, the above method can be applied to, but not limited to, scenarios such as MRI, synchronized EEG functional magnetic resonance imaging, and speech signal processing. For example, the first-type channels mentioned above can be used to receive an effective signal, and to receive or induct interference signal; the second-type channels can only be used to receive interference signal. However, the first calibration data and the second calibration data mentioned above only comprise interference signal, which is relatively pure interference signal. Thus, the first calibration data and the second calibration data can be used to estimate the coupling relationship between the first-type channels and the second-type channels of the interference signal. Furthermore, based on this coupling relationship, the interference signal of the practical measurement signal is estimated and removed, so as to eliminate the influence of the interference signal on the effective signal. For example, in an MRI scenario, the measurement signal mentioned above comprises mixed MRI signals and EMI signals, for example, the first calibration data and the second calibration data mentioned above can be calibration data 1 and calibration data 2 below, respectively; the effective signal and the first interference signal of the measurement signal mentioned above can be MRI signal and EMI signal 1, respectively; however the second interference signal can be EMI signal 2 below. Specifically, in the MRI scenario, the EMI signals of the measurement signal can be estimated and removed according to the interference cancellation method described above, so as to eliminate the influence of EMI signals on MRI signals. Furthermore, artifacts in MRI can be eliminated, the quality of MRI can be improved, and low-field MRI device can be operated normally in unshielded or partially shielded environments.

In one possible implementation of the first aspect described above, the coupling relationship mentioned above is used to represent the frequency domain correlation between the interference signal in the first-type channels and the second-type channels, and the coupling relationship is continuous and smooth in the frequency domain. For example, the coupling relationship mentioned above can be expressed by frequency domain dependent coupling function, the coupling function can refer to the coupling function F in the below.

In one possible implementation of the first aspect described above, the method further comprises: obtaining a coefficient $c_{i,j}$ according to a formula $$s_{r,t}=\sum_{j=t-K}^{t+K}\sum_{i=1}^{M}c_{i,j}s_{i,j}$$

and the first calibration data and the second calibration data, the coefficient $c_{i,j}$ is used to express the coupling relationship, and the coefficient $c_{i,j}$ is a time-invariant convolution kernel coefficient; wherein a size of the convolution kernel is 2K+1, that is the size of the convolution kernel is odd, K is a natural number, and $s_{r,t}$ is the t-th sampling data of the r-th first-type channel in the first calibration data, $s_{i,j}$ is the j-th sampling data of the i-th second-type channel in the second calibration data, the electronic device includes M second-type channels and N first-type channels, i takes a positive integer with a value of 1 to M, and r takes a positive integer with a value of 1 to N. For example, the size of the convolution kernel can be used to represent the product of the number of the rows of the matrix and the number of the columns of the matrix corresponding to the convolution kernel.

In one possible implementation of the first aspect described above, obtaining the coefficient $c_{i,j}$ according to the formula $$s_{r,t}=\sum_{j=t-K}^{t+K}\sum_{i=1}^{M}c_{i,j}s_{i,j}$$

(that is the formula (1) hereinafter) and the first calibration data and the second calibration data, comprises: according to the formula $$s_{r,t}=\sum_{j=t-K}^{t+K}\sum_{i=1}^{M}c_{i,j}s_{i,j},$$

for each sampling data of the r-th first-type channel in the first calibration data, obtaining an equation with the convolution kernel coefficient unknown, respectively, and obtaining a system of linear equations by combining all the equations, and obtaining the coefficient $c_{i,j}$ by solving the system of linear equations.

In one possible implementation of the first aspect described above, estimating the first interference signal in the measurement signal according to the coupling relationship between the first calibration data and the second calibration data and based on the second interference signal, comprises: estimating the second interference signal according to the formula $$s'_{r,t}=\sum_{j=t-K}^{t+K}\sum_{i=1}^{M}c_{i,j}s'_{i,j}$$

(that is the formula (2) hereinafter) and the coefficient $c_{i,j}$ and the first interference signal; wherein $s'_{r,t}$ is the t-th sampling data of the r-th first-type channel in the second interference signal, and $s'_{i,j}$ is the j-th sampling data of the i-th second-type channel in the first interference signal. It is understood that as the coupling relationship between the second interference signal and the first interference signal in each channel, is consistent with the coupling relationship between the first calibration data and the second calibration data in each channel, the formula (1) and the formula (2) have the same coefficient $c_{i,j}$.

In one possible implementation of the first aspect described above, the electronic device is MRI device, the effective signal is MRI signal, the interference signal includes at least one of the EMI signal and the thermal noise; the first-type channels (that is the receiving coil channel hereinafter) are implemented by one or more phased array coils; the second-type channels (that is the induction coil channel hereinafter) are implemented by one or more phased array coils, or by one or more electrodes attached to a surface of a detection object, such as human skin.

In one possible implementation of the first aspect described above, the electronic device is a synchronous EEG-functional magnetic resonance imaging device, the effective signal is an EEG signal, and the interference signal includes at least one of the radio frequency signals and gradient signals generated by the magnetic resonance imaging device; the first-type channels are implemented by one or more electrodes attached to the surface of the detection object (such as the human brain); the second-type channels are implemented by one or more electrodes attached to the surface of the detection object (such as the scalp or human body), or by one or more phased array coils (induction coils hereinafter).

In one possible implementation of the first aspect described above, the electronic device is a magnetic resonance imaging device comprising a transmitting coil, and the preset state is to close the transmitting coil; the method further comprises: in the case of the preset state, the signal collected from the first-type channels acts as the first calibration data, and the signal collected from the second-type channels acts as the second calibration data; the RF signal transmitted by the transmitting coil is used to excite the first-type channels to receive the effective signal. The RF signal transmitted by the transmitting coil is used to excite the receiving coil channel to receive the magnetic resonance imaging signal, which is mainly dominated by electromagnetic interference. When the transmitting RF coil is closed, the transmitting RF coil will not generate a magnetic resonance imaging signal, so the signals in the first-type and second-type channels are only electromagnetic interference signals.

In one possible implementation of the first aspect described above, the preset state is that the signal in the first-type channels and the second-type channels is collected multiple times; the method further comprises: in the case of the preset state, the first signal acts as the first calibration data and the second signal acts as the second calibration data; wherein the first signal is the difference between signals collected successively from the first-type channels, and the second signal is the difference between the two signals collected successively from the second-type channel in the first interference signal. It is understood that for low-field magnetic resonance imaging device, magnetic resonance signals can be collected multiple times to improve the signal-to-noise ratio. Specifically, for the signals collected by magnetic resonance imaging device for many times, it can be considered that the two magnetic resonance signals collected adjacently are theoretically unchanged, while the electromagnetic interference signals are randomly changed. By subtracting one collected signal from the other collected signal that is adjacent, the electromagnetic interference signal can be retained as calibration data and the magnetic resonance signal can be eliminated to the greatest extent.

In one possible implementation of the first aspect described above, the electronic device is a magnetic resonance imaging device comprising a gradient coil, and the preset state is in the dead time during the collection of the measurement signal and the second interference signal; in the case of preset state, using the crusher gradient to damage effective signal from the gradient coil, to make the signal collected from the first-type channels act as the first calibration data, and make the signal collected from the second-type channels act as the second calibration data; the dead time is the interval time used to wait for the lateral or longitudinal magnetization vector until it returns to its original state when the magnetic resonance imaging device performs the magnetic resonance imaging.

In one possible implementation of the first aspect described above, the electronic device is a magnetic resonance imaging device comprising a transmitting coil, and the preset state is that the high-frequency part of the signal in the frequency domain space (i.e., k-space) in the signal collected from the first-type and second-type channels is dominated by electromagnetic interference; the method further comprises, the high-frequency part of the signal in the frequency domain space of the measurement signal acts as the first calibration data, and the high-frequency part of the signal in the frequency domain space of the second interference signal acts as the second calibration data.

In one possible implementation of the first aspect described above, the effective signal and interference signal are one-dimensional or multi-dimensional data, and the convolution kernel is one-dimensional or multi-dimensional convolution kernel. Moreover, the dimension of the signal is consistent with the dimension of the convolution kernel.

In the second aspect of the present application, there is provided an interference cancellation device applied to an electronic device including first-type and second-type channels having a signal reception function, comprising: a collecting module for collecting, from the first-type channels, a measurement signal in which an effective signal and a first interference signal are mixed, and collecting a second interference signal from the second-type channels; an estimation module for estimating the first interference signal in the measurement signal according to the coupling relationship between the first calibration data and the second calibration data and based on the second interference signal collected; a removal module for removing the first interference signal from the measurement signal to obtain the target effective signal; wherein, the first calibration data and the second calibration data are the interference signals collected from the first-type and second-type channels when the electronic device is in a preset state. For example, the collecting module, the estimation module, and the removal module can be implemented by a processor, which has the functionality of these modules or units, of an electronic device.

In one possible implementation of the second aspect described above, the coupling relationship is used to express the frequency domain correlation between the interference signals in the first-type channels and the second-type channels, and the coupling relationship is continuous and smooth in the frequency domain.

In one possible implementation of the second aspect described above, the device further comprises: a determining module, for obtaining a coefficient $c_{i,j}$ according to the formula $$s_{r,t} = \sum_{j=t-K}^{t+K} \sum_{i=1}^{M} c_{i,j} s_{i,j}$$

and the first calibration data and the second calibration data, the coefficient $c_{i,j}$ is a time-invariant convolution kernel coefficient; wherein, the size of the convolution kernel is 2K+1, K is the natural number, $s_{r,t}$ is the t-th sampling data of the r-th first-type channel in the first calibration data, $s_{i,j}$ is the j-th sampling data of the i-th second-type channel in the second calibration data, the electronic device includes M second-type channels and N first-type channels, i tales a positive integer with a value of 1 to M, r takes a positive integer with a value of 1 to N. For example, the determining module can be achieved by a processor, which has the function of the module or unit, of an electronic device.

In one possible implementation of the second aspect described above, the determining module, according to the formula $$s_{r,t} = \sum_{j=t-K}^{t+K} \sum_{i=1}^{M} c_{i,j} s_{i,j},$$

for each sampling data of the r-th first-type channel in the first calibration data, obtaining an equation with the convolution kernel coefficient unknown, respectively, and obtaining a system of linear equations by combining all the equations, and obtaining the coefficients $c_{i,j}$ by solving the system of linear equations.

In one possible implementation of the second aspect described above, estimating the first interference signal in the measurement signal according to the coupling relationship between the first calibration data and the second calibration data and based on the second interference signal, comprising: estimate the second interference signal according to the formula $$s'_{r,t} = \sum_{j=t-K}^{t+K} \sum_{i=1}^{M} c_{i,j} s'_{i,j}$$

and the coefficient $c_{i,j}$ and the first interference signal; wherein $s'_{r,t}$ is the t-th sampling data of the r-th first-type channel in the second interference signal, and $s'_{i,j}$ is the j-th sampling data of the i-th second-type channel in the first interference signal.

In one possible implementation of the second aspect described above, the electronic device is a magnetic resonance imaging device, the effective signal is a magnetic resonance imaging signal, and the interference signal includes at least one of the electromagnetic interference signal and thermal noise; the first-type channels are implemented by one or more phased array coils; the second-type channels are implemented by one or more phased array coils, or by one or more electrodes attached to the surface of the detection object.

In one possible implementation of the second aspect described above, the electronic device is a synchronous EEG-functional magnetic resonance imaging device, the effective signal is an EEG signal, and the interference signal includes at least one of the radio frequency signal and gradient signal generated by the magnetic resonance imaging device; the first-type channels are implemented by one or more electrodes attached to the surface of the detection object; the second-type channels are implemented by one or more electrodes attached to the surface of the detection object, or by one or more phased array coils.

In one possible implementation of the second aspect described above, the above electronic device is a magnetic resonance imaging device comprising a transmitting coil, and the preset state is to close the transmitting coil; the method further comprises: in the case of the preset state, the signal collected from the first-type channels acts as the first calibration data, and the signal collected from the second-type channels acts as the second calibration data; wherein, the RF signal transmitted by the transmitting coil is used to excite the first-type channels to receive an effective signal.

In one possible implementation of the second aspect described above, the preset state is that the signal in the first-type channels and the second-type channels is collected multiple times; the device further comprises: in the case of a preset state, the first signal acts as the first calibration data and the second signal acts as the second calibration data; wherein the first signal is the difference between two signals collected successively from the first-type channels, and the second signal is the difference between two signals collected successively from the second-type channels in the first interference signal.

In one possible implementation of the second aspect described above, the electronic device is a magnetic resonance imaging device comprising a gradient coil, and the preset state is in the dead time during the collection of the measurement signal and the second interference signal; in the case of preset state, using the crusher gradient to damage effective signal from the gradient coil, to make the signal acquired from the first-type channels act as the first calibration data, and make the signal collected from the second-type channels act as the second calibration data; the dead time is the interval time used to wait for the lateral or longitudinal magnetization vector until it returns to its original state when the magnetic resonance imaging device performs the magnetic resonance imaging.

In one possible implementation of the second aspect described above, the electronic device is a magnetic resonance imaging device comprising a transmitting coil, and the preset state is that the high-frequency part of the signal in the frequency domain space in the signal collected from the first-type channels and second-type channels is dominated by electromagnetic interference; the device further comprises: the high-frequency part of the signal in the frequency domain space of the measurement signal acts as the first calibration data, and the high-frequency part of the signal in the frequency domain space of the second interference signal acts as the second calibration data.

In one possible implementation of the second aspect described above, the effective signal and interference signal are one-dimensional or multi-dimensional data, and the convolution kernel is one-dimensional or multi-dimensional convolution kernel. Moreover, the dimension of the signal is consistent with the dimension of the convolution kernel.

In a third aspect of the present application, there is provided a computer-readable storage medium on which instructions are stored on the storage medium to make the computer perform the interference elimination method in the first aspect described mentioned above when the instructions are executed on the computer.

In a fourth aspect of the present application, there is provided an electronic device, comprising: one or more processors; one or more memories; the one or more memories store one or more programs, when the one or more programs are executed by the one or more processors, the electronic device performs the interference cancellation method in the first aspect mentioned above.

DETAILED DESCRIPTION

Figure 1:
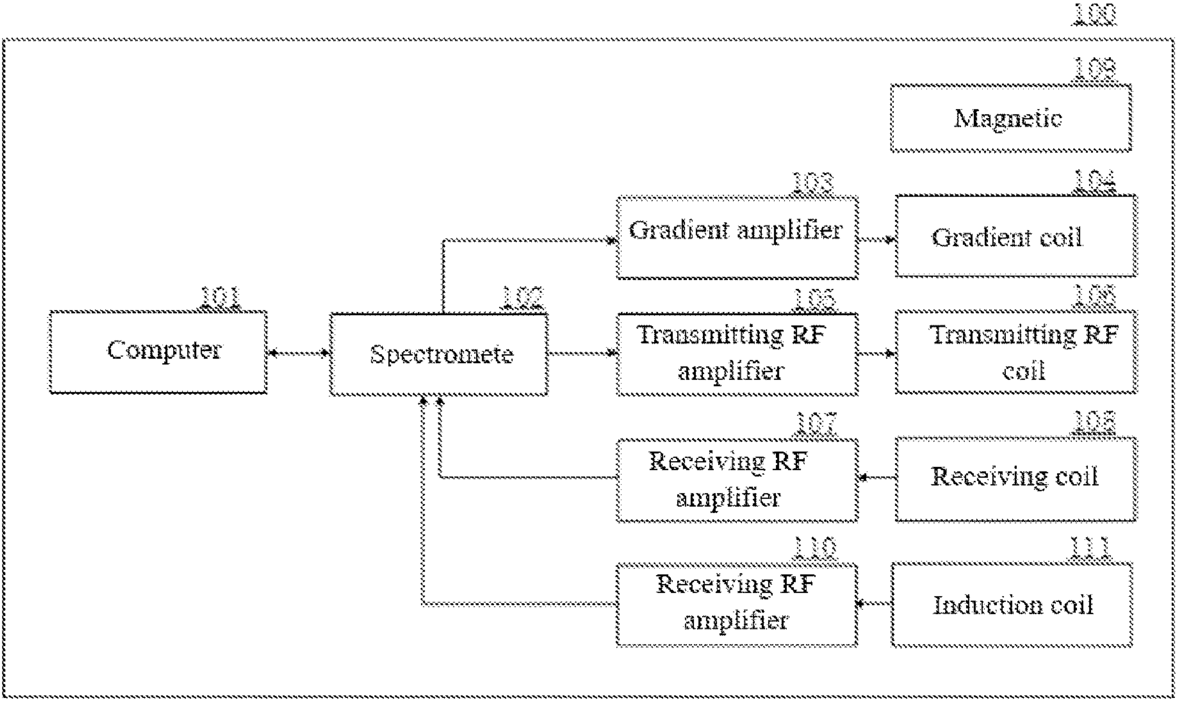
FIG. 1 shows schematic view of a structure of a magnetic resonance imaging device according to the embodiments of the present application.

Illustrative embodiments of the present application include, but are not limited to, an interference cancellation method, a medium, and a device.

The interference cancellation method provided by the embodiment of the present application may be applied to scenarios such as magnetic resonance imaging (MRI), synchronous EEG functional magnetic resonance imaging, and speech signal processing, but not limited to this. Specifically, electronic devices may include a plurality of channels with signal reception functions to eliminate interference signal from the measurement signal of multiple channels, thereby obtaining effective signal that is not affected by interference signal, the effective signal could be magnetic resonance imaging signals, EEG signals, voice signals, etc., as mentioned in the aforementioned applications.

As an example, in an MRI scenario, the effective signal can be an MRI signal, while the interference signal can be thermal noise or an electromagnetic interference signal (EMI) in the environment, etc. At this point, the electronic device can be a device with magnetic resonance imaging capabilities, which is referred to in this text as a magnetic resonance imaging device.

As another example, in a synchronized EEG function MRI scenario, effective signal can be EEG signal, while interfering signal can include magnetic resonance imaging RF signal and gradient signal generated during the operation of electronic device. At this point, the above mentioned electronic device can be a device with synchronous EEG functional magnetic resonance imaging, which can be referred to in this text as an EEG imaging device.

As another example, in a speech signal processing scenario, the effective signal can be the voice signal to be processed, while the interference signal can be ambient noise, and so on. In this case, the above mentioned electronic device may be a device with voice processing functions, for example, an electronic device equipped with voice assistant software. As an example, electronic device in this scenario may include, but are not limited to: mobile phones, smart speakers, tablets, laptops, desktop computers, ultra-mobile personal computers (UMPCs), netbooks, as well as cellular phones, personal digital assistants (PDAs), and augmented reality (AR), virtual reality (VR) devices, etc.

The following embodiments mainly take the execution of the interference cancellation method by the magnetic resonance imaging device in the magnetic resonance imaging scene as an example, and the interference cancellation method provided in the embodiment of the present application is explained. Similarly, the implementation details of the interference cancellation method performed by electronic devices in other application scenarios will not be described in this text, and some descriptions can be referred to the relevant descriptions of the interference cancellation methods performed on magnetic resonance imaging device.

Magnetic resonance imaging can generate medical images for disease diagnosis in medical or clinical applications. Specifically, magnetic resonance imaging technology can use the signal generated by the resonance of the nucleus in a strong magnetic field to reconstruct the image, and make body tomographic images of cross-sectional, sagittal, coronal and various inclined planes of objects such as the human body.

In the implementation of the present application, the magnetic resonance imaging device may be a low-field, ultra-low-field magnetic resonance imaging device, or a medium-field and high-field magnetic resonance imaging device. As an example, magnetic resonance imaging systems in clinical applications can often be divided into high field (above 1 T), medium field (0.3-1 T), low field (0.1-0.3 T), and ultra-low field (below 0.1 T) by magnetic field strength.

It is understood that magnetic resonance imaging device usually needs to be deployed in a specific room or area of a hospital or research institution to achieve strict electromagnetic shielding, which is a large device with high cost and complex structure, which is limited by the site of use and cannot be used as a general imaging device. Regardless of the location of deployment, such as not limited to use in hospitals or research institutions, the use of small magnetic resonance imaging device that is mobile and low-cost will greatly expand the application of magnetic resonance imaging.

More specifically, the embodiment of the present application is mainly applied to low-field or ultra-low-field magnetic resonance imaging device, eliminating interference signals such as environmental electromagnetic interference signals during the magnetic resonance imaging process, thereby eliminating artifacts existing in magnetic resonance imaging, improving the quality of magnetic resonance imaging, and realizing normal operation of low-field magnetic resonance imaging in an unshielded or partially shielded environment. In this way, because the magnetic resonance imaging device does not require strict electromagnetic shielding, that is, there is no need to place the magnetic resonance imaging device in the shielding room, so there is no need to build a special shielding room, the installation is simple, and the cost can be greatly reduced. Moreover, the application scenarios of magnetic resonance imaging can be greatly expanded, for example, in point-of-care MRI (POC MRI), emergency rooms (ICU), or medical vehicles and ambulances.

According to some embodiments of the present application, one or more multichannel coils commonly used in magnetic resonance parallel imaging (e.g., phased array coils) can be used, or one or more electrodes may be attached to the surface of human skin to receive signals. Functionally, the above coils or electrodes can be divided into two categories. A category of coil, called a receiving coil, is used to receive magnetic resonance signals (specifically magnetic resonance imaging signals), and should avoid receiving interference signal such as electromagnetic interference signal or thermal noise in the environment. Specifically, in the actual application process, due to the lack of electromagnetic shielding of low-field magnetic resonance imaging device, the receiving coil will inevitably be affected by electromagnetic interference, that is, the receiving coil will also receive some electromagnetic interference signals. The other category of coil, called the sensing coil, is used to sense environmental electromagnetic interference signal, which can also be achieved with electrodes.

The embodiments of the present application will be further described in detail in conjunction with the accompanying drawings.

As shown in FIG. 1, a schematic view of a possible structure of a magnetic resonance imaging device provided for an embodiment of the present application. The magnetic resonance imaging device 100 may include: a computer 101, a spectrometer 102, a gradient amplifier 103, a gradient coil 104, a transmitting RF amplifier 105, a transmitting RF coil (also referred to as a transmitting coil) 106, a receiving RF coil 107, a receiving RF amplifier (also referred to as a receiving coil) 108, a magnet 109, an induction coil 101 and a receiving RF amplifier 110.

In particular, the computer 101 is used to issue instructions to the spectrometer 102 under the control of the operator, to trigger the spectrometer 102, according to the instructions, to generate a waveform of the gradient signal and a waveform of the radio frequency signal. The gradient signal generated by the spectrometer 102 is amplified by the gradient amplifier 103, and the gradient coil 104 forms a gradient of the magnetic field, thereby realizing spatial gradient coding for the magnetic resonance signal (specifically the magnetic resonance imaging signal). Specifically, spatial gradient coding is used to spatially locate magnetic resonance signals, that is, to distinguish the location of sources of magnetic resonance signals. The RF signal generated by the spectrometer 102 is amplified by the transmitting RF amplifier 105, and emitted by the transmitting RF coil 106, thereby excitation of protons (hydrogen nuclei) in the imaging region. Wherein the excited proton may emit a radio frequency signal, the RF signal may be received by the receiving coil 108, and amplified by the receiving RF amplifier 107, and then converted into a digital signal by the spectrometer 102, and then transmitted to the computer 101 for processing to obtain an image and display. Further, magnet 109 may be any suitable type of magnet capable of generating a principal magnetic field. The induction coil 101 is used to sense electromagnetic interference signals in the environment, and after amplification by the receiving RF amplifier 110, it is converted into a digital signal by the spectrometer 102 and transmitted to the computer 101 for processing.

In some embodiments, when designing the receive coil and the induction coil, it is necessary to maximize the signal-to-noise ratio that the coil can provide. That is, for the receiving coil, it should be able to receive magnetic resonance signal (specifically magnetic resonance imaging signal) as sensitively as possible, and be affected by electromagnetic interference and thermal noise as little as possible. For induction coils, it should be able to perceive environmental electromagnetic interference as sensitively as possible, receive as little magnetic resonance signal as possible, and be affected by thermal noise as little as possible.

In addition, in some embodiments, both categories of coils need to minimize the influence of thermal noise, for example, in practical applications, the coil resistance can be minimized by some cooling devices using cooling, thereby reducing the influence of thermal noise. It is understood that the embodiment of the present application does not specifically describe the cooling device, and may refer to any achievable method in the relevant technology.

Similarly, the EEG imaging device in the embodiment of the present application may also include a transmitting coil 106 and a receiving coil 108 illustrated in FIG. 1 for generating magnetic resonance imaging RF signals based on the same process; A gradient coil 104 may also be included for generating a gradient signal.

In some embodiments, the above receiving coil and induction coil may be implemented using one or more phased array coils widely used in modern medical magnetic resonance imaging. In addition, the scanning object is a human body, and the induction coil can also be replaced with an electrode attached to the surface of human skin, in which the electrode can be used to sense the electromagnetic interference signal received by the human body, thereby eliminating the electromagnetic interference signal in the measurement signal of the receiving coil.

It is understood that in the embodiment of the present application, the magnetic resonance imaging device 100 relates to a plurality of channels having a signal reception function, in which the plurality of channels may include a plurality of channels of a single phased array coil, may also include a plurality of channels of a plurality of coils, the present application is not specifically limited in this regard. Further, in an embodiment of the present application, the design, layout (deployment location, deployment direction, and the like). of the receiving coil and induction coil in the magnetic resonance imaging device 100 is not specifically limited, and can be any achievable solution.

More specifically, in some embodiments of the present application, for the magnetic resonance imaging device 100, the channel in the receiving coil may be referred to as the receiving coil channel. The greater the number of channels of the receiving coil, it will be beneficial to improve the signal-to-noise ratio (SNR) of the magnetic resonance signal received by the receiving coil, or make the receiving coil provide parallel imaging capabilities. In an embodiment of the present application, a plurality of channels of the receiving coil may also be used to enhance its ability to identify and eliminate electromagnetic interference signal. The channels in the induction coil can be called as the induction coil channel. The more channels of the induction coil, the more accurate it is to depict the characteristics of the electromagnetic interference signal, so as to accurately estimate the electromagnetic interference signal received by the receiving coil through the electromagnetic interference signal received by the induction coil.

For example, the magnetic resonance imaging device 100 illustrated in FIG. 1 may provide a receiving coil and an induction coil, and the receiving coil has one channel, and the induction coil has two channels, but is not limited thereto. At this time, the magnetic resonance imaging device 100 provides a plurality of channels including receiving coil channel(s) and induction coil channel(s).

Similarly, in a synchronous EEG functional magnetic resonance imaging scenario, the plurality of channels with signal reception function provided by the EEG imaging device can be realized by electrodes attached to the scalp. And, in a speech signal processing scenario, a plurality of channels provided by an electronic device can be a plurality of analog signal channels provided by a plurality of microphones.

In an embodiment of the present application, the magnetic resonance imaging device 100 shown in FIG. 1, may collect measurement signal from the receiving coil channel and the induction coil channel, and obtain calibration data from these channels. Furthermore, according to the calibration data, the electromagnetic interference signal in the actual collected measurement signal can be estimated by convolution operation to achieve electromagnetic interference cancellation.

The calibration data includes only the electromagnetic interference signal from the receiving coil channel and the induction coil channel of the magnetic resonance imaging device 100. That is, the above calibration data is a relatively pure electromagnetic interference signal, which can be used to estimate the coupling relationship between the electromagnetic interference signals received by different channels.

In some embodiments, the calibration data is the electromagnetic interference signals collected from the receiving coil channel and induction coil channel when the magnetic resonance imaging device 100 is in a preset state.

In some embodiments of the present application, the magnetic resonance imaging device 100 may obtain calibration data in the following four ways:

(1) Pre-Scan Method:

when the magnetic resonance imaging device 100 is in the case of closing the transmitting coil (i.e., the transmitting RF coil 106), measurement signal is obtained from the receiving coil channel and the induction coil channel and is used as calibration data. The radio frequency signal emitted by the transmitting coil is used to excite the nuclei (such as hydrogen nuclei) in the imaging object, and the excited nucleus emits a magnetic resonance imaging signal, which is in turn received by the receiving coil channel. If the transmitting coil is turned off, the measurement signal received by the receiving coil does not contain an MRI signal and consists entirely of electromagnetic interference and thermal noise. In particular, the magnetic resonance imaging device 100 may turn off, before or after the collection of the magnetic resonance imaging signal, the transmitting RF coil (then the receiving RF coil will not receive the magnetic resonance imaging signal), to collect the above calibration data. However, this method has two major drawbacks, one is that it will extend the total scanning time of the magnetic resonance imaging device 100; furthermore, if the EMI signal in the environment changes, or if the coupling relationship between channels of the signals changes due to the movement of the scanned object (such as the human body), the calibration data cannot be used to accurately estimate the coupling relationship between the channels of the EMI signal during a formal MRI scan. At this time, the preset state is the magnetic resonance imaging device 100 with the closed transmitting coil 106.

It should be noted that the coupling relationship between the plurality of channels in the electromagnetic interference signal of the magnetic resonance imaging device 100, specifically the frequency domain correlation between the plurality of channels of the electromagnetic interference signal, is continuous and smooth in the frequency domain. It is understood that the frequency domain correlation between multiple channels of electromagnetic interference signal can be expressed as the linear relationship of electromagnetic interference signals received by each channel at different frequency points.

Specifically, the coupling relationship can be represented by a frequency-domain dependent coupling function that is continuous and smooth in the frequency domain. As an example, in an embodiment of the present application, in the case of a plurality of channels of the magnetic resonance imaging device 100 including a receiving coil channel and an induction coil channel, according to the electromagnetic interference signal $C_{sen}$ sensed by the induction coil channel contained in the calibration data, and the electromagnetic interference signal $C_{rec}$ received by the receiving coil channel, the coupling function F is estimated, such that $F(C_{sen})=C_{rec}$. Subsequently, when the magnetic resonance imaging device 100 formally collects signal from the receiving coil channel, according to the electromagnetic interference signal $S_{sen}$ induced by the induction coil channel and the coupling function F, the electromagnetic interference signal $S_{rec}$ received by the receiving coil channel can be estimated, such that $S_{rec}=F(C_{sen})$.

(2) Multiple Acquisition Difference Method:

in the case of the signals of a plurality of channels of the magnetic resonance imaging device 100 are collected multiple times, the difference between two (or more) signals collected successively from multiple channels act as calibration data. Specifically, the magnetic resonance imaging device 100, makes the difference between two signals collected successively from the receiving coil channels be as part of the calibration data, and makes the difference between the two signals collected successively from the receiving coil channels be as another part of the calibration data.

It is understood that low-field magnetic resonance imaging devices can collect magnetic resonance signals multiple times to achieve magnetic resonance imaging. Specifically, for the signals collected by magnetic resonance imaging device for many times, it can be considered that the two magnetic resonance signals collected adjacently are theoretically unchanged, while the electromagnetic interference signals are randomly changed; by subtracting one collected signal from the other collected signal that is adjacent, the electromagnetic interference signal can be retained as calibration data and the magnetic resonance signal can be eliminated to the greatest extent.

However, if there is magnetic drift (which further causes the change of the phase), or the motion of the scanned object (or detected object), or the presence of a free induction decay (FID) signal in fast spin echo (FSE) imaging using phase cycling, these will result in the magnetic resonance signal obtained from multiple scans not being eliminated to the greatest extent. This affects the estimation of the coupling relationship.

(3) Built-In Scanning Method:

magnetic resonance imaging device 100, in the dead time during the actual collection of signals from a plurality of channels, uses a crusher gradient from the gradient coil to damage magnetic resonance imaging signal, and collects a measurement signal from a plurality of channels, and makes the measurement signal as calibration data. The dead time is the interval time used to wait for the lateral or longitudinal magnetization vector until it returns to its original state when the magnetic resonance imaging device performs the magnetic resonance imaging. Specifically, the calibration data includes a measurement signal collected from the receiving coil channel and a measurement signal collected from the induction coil channel. The preset state may be the dead time during which the magnetic resonance imaging device 100 collects the signal.

It is understood that the use of dead time during the scanning process to collect calibration data can avoid the problems in (1) and (2) mentioned above, but the scan sequence needs to be modified, which will also increase the amount of data to be collected and increase the difficulty of subsequent calculations. Specifically, for data collection in the phase of the dead time, it is also necessary to open the gradient coil to generate a readout gradient. Before formal data collection, a crusher gradient needs to be added to the gradient coil, which minimizes the component of the magnetic resonance imaging signal in the calibration data. As an example, for fast spin echo (FSE), the echo train length (ETL) can be extended, and for the late readout gradient mentioned above, the transmitting RF coil can be turned off (i.e., the 180-degree reunited RF pulse can be turned off) to obtain the calibration data.

(4) Using the High-Frequency Part of the K Space:

the magnetic resonance imaging device 100 make the high-frequency part of the signal in the frequency domain space collected from a plurality of channels be as calibration data. At this point, the calibration data includes the signal collected from the receiving coil channel as well as the signal collected from the induction coil channel.

It is understood that the high-frequency part of the frequency domain space (i.e. k-space) has a weak magnetic resonance imaging signal, and it can be considered that the signal in this part is dominated by electromagnetic interference, so that this part of the data is used as calibration data.

Figure 2:
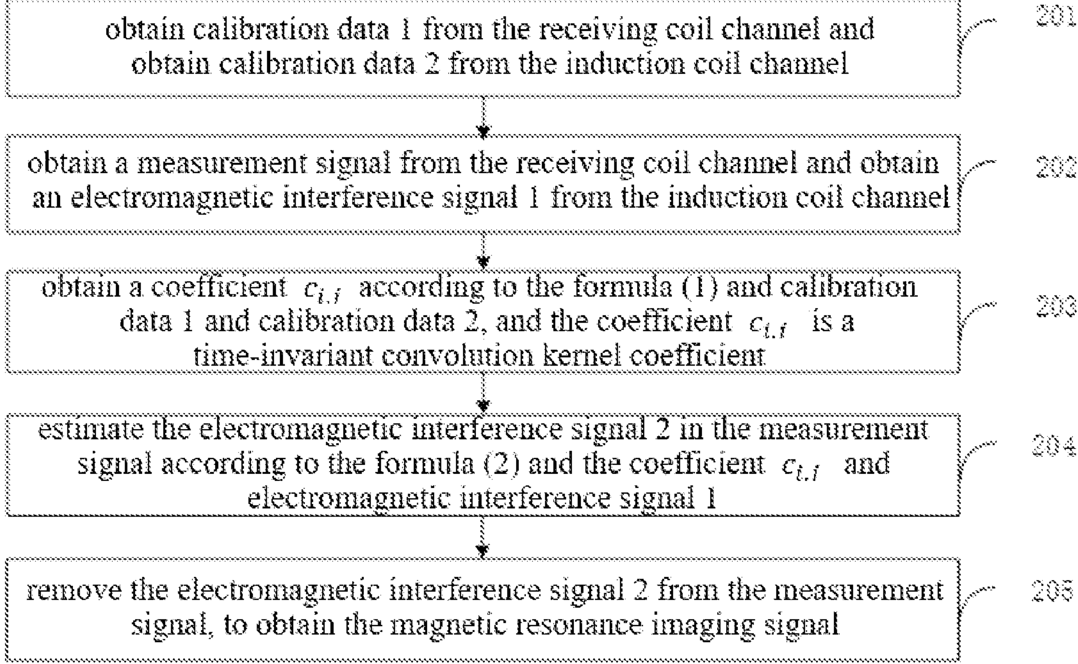
FIG. 2 shows a schematic flow diagram of an interference cancellation method according to the embodiments of the present application.

Based on the above description, the following details are the main workflow of the MRI device 100 performing the interference cancellation method. Specifically, the technical details described in the magnetic resonance imaging device 100 shown above for FIG. 1 are still applicable in the following method flow, in order to avoid duplication, some of them will not be repeated. In some embodiments, the subject of the interference cancellation method of the present application may be the magnetic resonance imaging device 100, specifically the computer 101 in the magnetic resonance imaging device 100. As shown in FIG. 2, an interference cancellation method flow provided for the present application may include steps of:

Step 201: the magnetic resonance imaging device 100 obtains calibration data 1 from the receiving coil channel and obtains calibration data 2 from the induction coil channel.

It is understood that the calibration data 1 and calibration data 2 act as a whole to be the calibration data collected from a plurality of channels by the magnetic resonance imaging device 100.

Step 202: the magnetic resonance imaging device 100 obtains a measurement signal from the receiving coil channel and obtains an electromagnetic interference signal 1 from the induction coil channel.

It is understood that the measurement signal and electromagnetic interference signal 1 act as a whole to be the signal collected from a plurality of channels by the magnetic resonance imaging device 100.

In some embodiments, for a low-field (or ultra-low-field) magnetic resonance imaging device 100, the measurement signal and electromagnetic interference signal 1 are collected from a plurality of channels for many times.

Step 203: the magnetic resonance imaging device 100 obtains, according to the formula $$s_{r,t}=\sum_{j=t-K}^{t+K}\sum_{i=1}^{M}c_{i,j}s_{i,j}$$

(that is, the formula (1)) and calibration data 1 and calibration data 2, the coefficient $c_{i,j}$, and the coefficient $c_{i,j}$ is a time-invariant convolution kernel coefficient.

The coefficient $c_{i,j}$ is used to represent the coupling relationship between the receiving coil channel and the induction coil channel of the the electromagnetic interference signal.

The size of the convolution kernel corresponding to the coefficient $c_{i,j}$ is 2K+1, that is, the size of the convolution kernel is odd, K is the natural number, $s_{r,t}$ is the t-th sampling data of the r-th receiving coil channel in calibration data 1, $s_{i,j}$ is the j-th sampling data of the i-th induction coil channel in calibration data 2, and the magnetic resonance imaging device 100 includes M induction coil channels and N receiving coil channels, and i takes a positive integer with a value of 1 to M. r takes a positive integer with a value of 1 to N. The size of the convolution kernel can be used to represent the product of the number of rows of the matrix and the number of the columns of the matrix corresponding to the convolution kernel.

Figure 3:
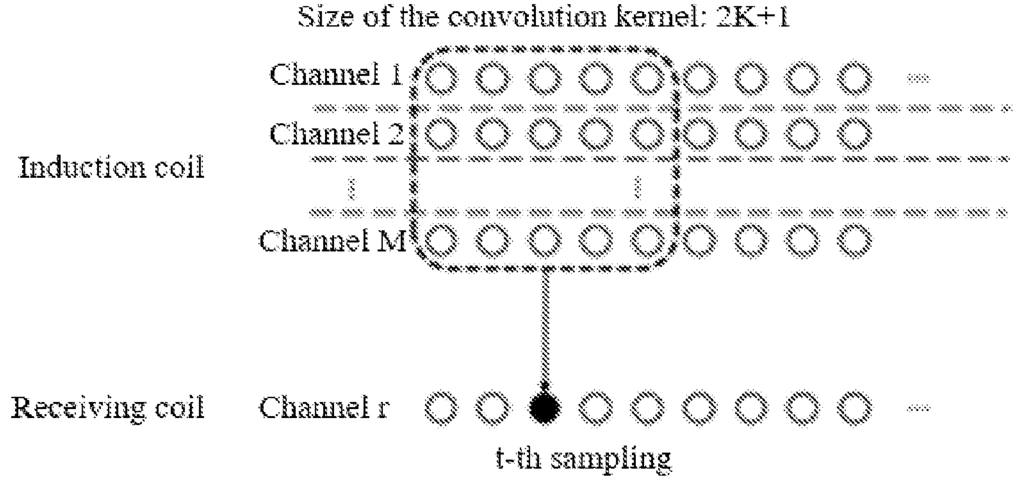
FIG. 3 shows a schematic diagram of a convolution kernel according to the embodiments of the present application.

For example, as shown in FIG. 3, a schematic diagram of a convolution kernel provided for the present application, the channel 1-channel M shown in FIG. 3 are induction coil channels provided by the induction coil, and channel r is a receiving coil channel provided by the receiving coil. Specifically, if the size of the convolution kernel is 2K+1, then the convolution kernel is a matrix with a size of (2K+1)×M. Assuming M=3, K=2, the matrix size of the convolution kernel is 5×3. In addition, the sampling data corresponding to one convolution kernel in channel 1-channel M corresponds to the t-th sampling data in channel r.

In some embodiments, the magnetic resonance imaging device 100 according to the formula $$s_{r,t} = \sum_{j=t-K}^{t+K} \sum_{i=1}^{M} c_{i,j} s_{i,j}$$

(1), for each sampling data of the r-th receiving coil channel in calibration data 1, obtains an equation with the convolution kernel coefficient unknown, and obtains a system of linear equations by combining all the equations, and obtains the coefficients $c_{i,j}$ by solving the system of linear equations.

Step 204: the magnetic resonance imaging device 100 according to the formula $$s'_{r,t} = \sum_{j=t-K}^{t+K} \sum_{i=1}^{M} c_{i,j} s'_{i,j}$$

(i.e., formula (2)) and coefficients $c_{i,j}$ and electromagnetic interference signal 1, estimate the electromagnetic interference signal 2 in the measurement signal.

$s'_{r,t}$ is the t-th sampling data of the r-th receiving coil channel in the electromagnetic interference signal 2, and $s'_{i,j}$ is the j-th sampling data from the i-th induction coil channel in the electromagnetic interference signal 1.

It is understood that as the coupling relationship between the electromagnetic interference signal 2 and the electromagnetic interference signal 1 in each channel, is consistent with the coupling relationship between the calibration data 1 and the calibration data 2 in each channel. Therefore, Equation (1) and Equation (2) have the same coefficient $c_{i,j}$.

Step 205: the magnetic resonance imaging device 100 removes the electromagnetic interference signal 2 from the measurement signal, to obtain the magnetic resonance imaging signal.

Thus, in an embodiment of the present application, the magnetic resonance imaging device 100 may obtain a convolution core based on the calibration data, and estimate the electromagnetic interference signal in the receiving coil based on the electromagnetic interference signal measured by the induction coil based on the convolution kernel, and eliminate the electromagnetic interference signal so as to eliminate the influence of electromagnetic interference signal on the magnetic resonance imaging signal, thereby improving the quality of magnetic resonance imaging.

Similarly, for other scenarios where embodiments of the present application are applied, the electronic device may also follow the steps similar to steps 201-205 mentioned above to implement the interference cancellation method, the difference is that the subject to be executed is different, the source of a plurality of channels is different, the type of the effective signal and type of the interference signal are different.

Further, in some other embodiments, the effective signal and the interference signal may also be one-dimensional data or multi-dimensional data (such as two-dimensional data). At this time, the convolution kernel used in the interference cancellation method can be one-dimensional or multi-dimensional convolution kernel, that is, the dimension of the signal is consistent with the dimension of the convolution kernel, and other processes are similar to the relevant description in steps 201-205 mentioned above, and will not be repeated.

Figure 4:
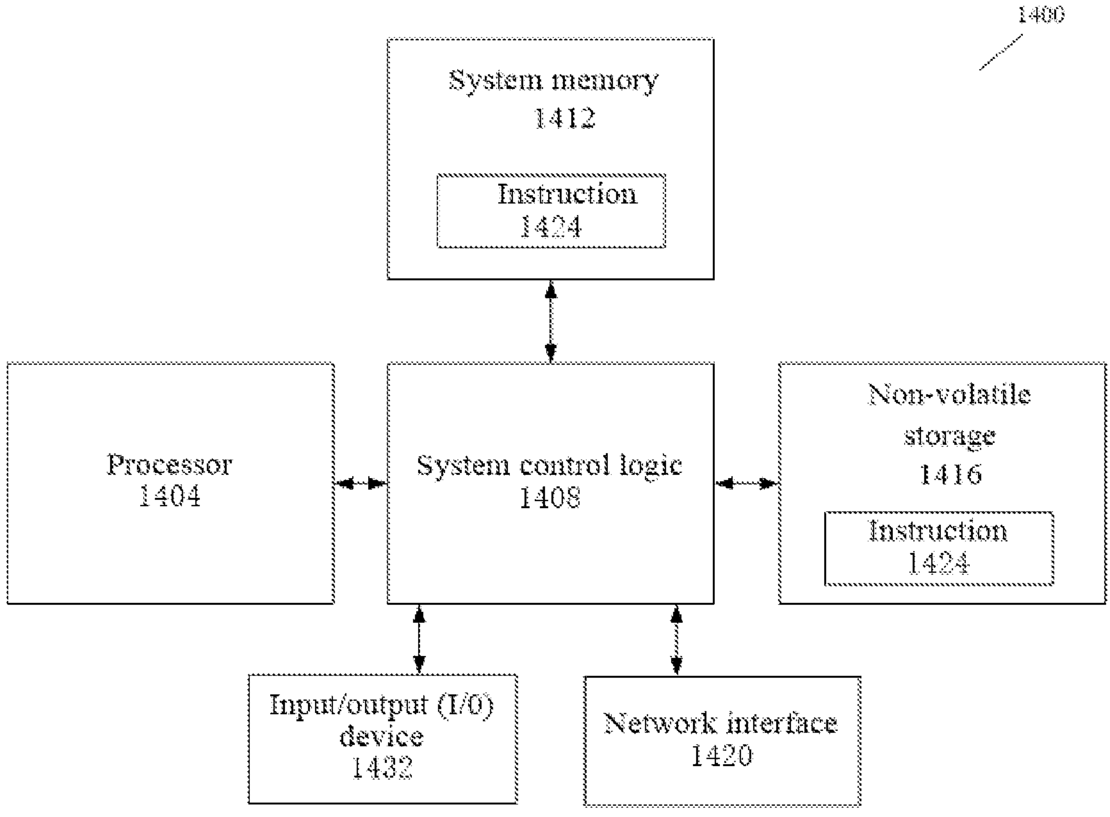
FIG. 4 shows a block diagram of a computer for an MRI device according to the embodiments of the present application.

Referring now to FIG. 4, a block diagram of a computer in a magnetic resonance imaging device 100 according to an embodiment of the present application. FIG. 4 schematically illustrates a computer 1400 according to a plurality of embodiments. In an embodiment, the system 1400 may include one or more processors 1404, a system control logic 1408 connected to at least one of the processors 1404, a system memory 1412 connected to the system control logic 1408, a non-volatile memory (NVM) 1416 connected to the system control logic 1408, and a network interface 1420 connected to the system control logic 1408.

In some embodiments, the processor 1404 may include one or more single-core or multi-core processors. In some embodiments, the processor 1404 may include any combination of general-purpose processors and specialized processors (e.g., graphics processors, application processors, baseband processors, etc.) In an embodiment, when the computer 1400 uses an eNB (Evolved Node B, Enhanced Base Station) 101 or RAN (Radio Access Network) controller 102, the processor 1404 may be configured to perform various compliant embodiments, for example, one or more of a plurality of embodiments as shown in FIG. 2. For example, the processor 1404 may estimate the interference signal in the actual measurement signal based on convolution operation on the calibration data from a plurality of channels, and then remove the interference signal in the measurement signal to obtain the final effective signal.

In some embodiments, the system control logic 1408 may include any suitable interface controller to provide any suitable interface to at least one of the processor 1404 and/or any suitable device or component communicating with the system control logic 1408.

In some embodiments, the system control logic 1408 may include one or more memory controllers to provide an interface connected to the system memory 1412. System memory 1412 may be used to load and store data and/or instructions. In some embodiments, the memory 1412 of the system 1400 may include any suitable volatile memory, such as a suitable dynamic random access memory (DRAM).

NVM/memory 1416 may include one or more tangible, non-transient computer-readable media for storing data and/or instructions. In some embodiments, NVM/memory 1416 may include flash memory and other arbitrary suitable non-volatile memory and/or any suitable non-volatile storage device, such as HDD (Hard Disk Drive), CD (Compact Disc) drive, DVD (Digital Versatile Disc) drive in at least one.

NVM/memory 1416 may include a portion of the storage resources on the device installed on the system 1400, or it may be accessed by the device, but not necessarily part of the device. For example, NVM/storage 1416 may be accessed via the network via the network interface 1420.

In particular, system memory 1412 and NVM/memory 1416 may include: a temporary copy and a permanent copy of instruction 1424, respectively. Instruction 1424 may include: instructions executed by at least one of the processors 1404, causing the computer 1400 to implement the method shown in FIG. 2. In some embodiments, instruction 1424, hardware, firmware, and/or its software components may be additionally/alternatively placed in the system control logic 1408, network interface 1420 and/or processor 1404.

Network interface 1420 may include a transceiver for providing a radio interface for the system 1400, and then communicate with any other suitable device (such as a front-end module, antenna, etc.) via one or more networks. In some embodiments, the network interface 1420 may be integrated into other components of the system 1400. For example, the network interface 1420 may be integrated in at least one of the processor 1404, system memory 1412, NVM/memory 1416, and the firmware device (not shown)

having instructions, when at least one of the processors 1404 executes the instructions, the computer 1400 implements the method shown in FIG. 2.

Network interface 1420 may further include any suitable hardware and/or firmware, to provide multiple-input multiple-output (MIMO) radio interface. For example, the network interface 1420 may be a network adapter, a wireless network adapter, a telephone modem and/or a wireless modem.

In one embodiment, at least one of the processors 1404 may be logically encapsulated with one or more controllers for system control logic 1408, to form a system in package (SiP). In an embodiment, at least one of the processors 1404 may be integrated on the same die with the logic of one or more controllers for system control logic 1408, to form a system-on-chip (SoC).

Computer 1400 may further include: input/output (I/O) device 1432. The I/O device 1432 may include a user interface enabling the user to interact with the system 1400; the interface of the peripheral component is designed such that the peripheral component can also interact with the computer 1400. In some embodiments, the computer 1400 further comprises a sensor for determining at least one of the environmental conditions and location information associated with the computer 1400.

In some embodiments, the user interface may include, but is not limited to, a display (e.g., liquid crystal display, touch screen display, etc.), speakers, microphones, one or more cameras (e.g., still image cameras and/or video cameras), flashlight (e.g., LED flash) and keyboard.

In some embodiments, peripheral component interfaces may include, but are not limited to, non-volatile memory ports, audio jacks, and power interfaces.

In some embodiments, the sensor may include, but is not limited to, a gyroscope sensor, an accelerometer, a proximity sensor, an ambient light sensor and a positioning unit. The positioning unit may also be part of the network interface 1420 or interact with the network interface 1420, so as to communicate with components of the positioning network (e.g., global positioning system (GPS) satellites).

Similarly, for the voice processing scenario applied by an embodiment of the present application, in some embodiments, the electronic device of the present application performing interference cancellation is a mobile phone, which is used as an example, describing the structure of the electronic device.

Figure 5:
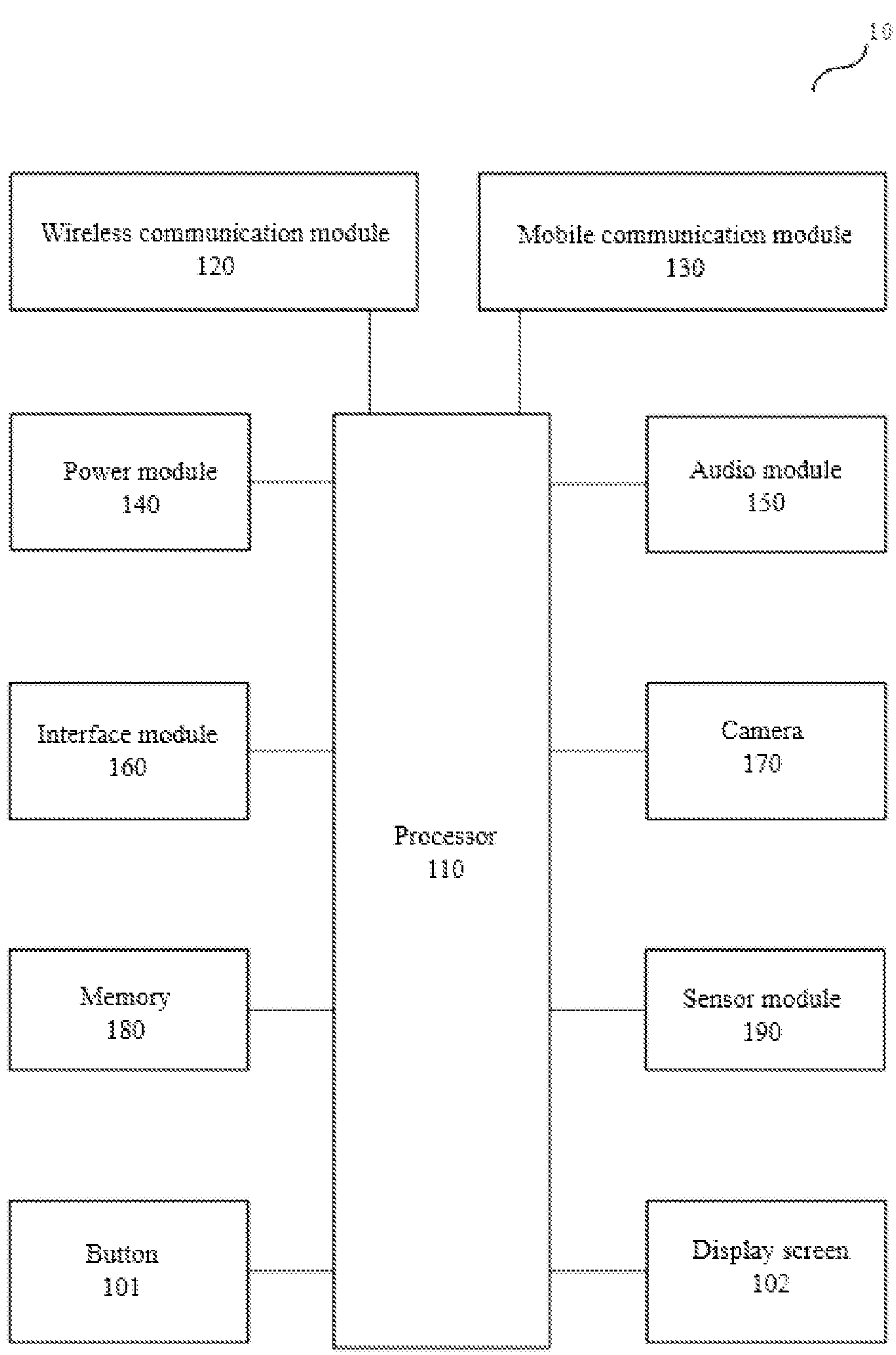
FIG. 5 shows a block diagram of a mobile phone according to the embodiments of the present application.

As shown in FIG. 5, the mobile phone 10 may include a processor 110, a power module 140, a memory 180, a mobile communication module 130, a wireless communication module 120, a sensor module 190, an audio module 150, a camera 170, an interface module 160, a button 101 and a display screen 102.

It is understood that the illustrative structure of embodiments of the present invention does not constitute a specific limitation of the mobile phone 10. In other embodiments of the present application, the mobile phone 10 may include more or less components than shown, or combination of certain components, or splitting certain components, or different component arrangements. The parts illustrated may be implemented by hardware, software, or a combination of software and hardware.

The processor 110 may include one or more processing units. The processor 110 may be provided with a memory unit for storing instructions and data. In some embodiments, the memory cell in the processor 110 is a cache memory 180. For example, the processor 110 may estimate, from a plurality of channels of calibration data, based on convolution operation, the interference signal in the actual measurement signal, and then remove the interference signal in the measurement signal to obtain the final effective signal.

Power supply module 140 may include a power supply, power management components, and the like. The power supply can be battery. The power management component is used to manage the charging of power supplies and the power supply to other modules.

Mobile communication module 130 may include, but is not limited to, antennas, power amplifiers, filters, LNA (Low noise amplify) and the like.

The wireless communication module 120 may include an antenna, and through the antenna to achieve the transmission and reception of electromagnetic waves. The mobile phone 10 can communicate with the network and other devices through wireless communication technology.

In some embodiments, the mobile communication module 130 and the wireless communication module 120 of the mobile phone 10 may also be located in the same module.

The display screen 102 is used to display the human-computer interaction interface, images, videos, etc., for example, for displaying the speech representation semantic information corresponding to the effective signal processed by the processor 110. Display 102 includes a display panel.

The sensor module 190 may include a proximity light sensor, a pressure sensor, a gyroscope sensor, a barometric pressure sensor, a magnetic sensor, an acceleration sensor, a range sensor, a fingerprint sensor, a temperature sensor, a touch sensor, an ambient light sensor, a bone conduction sensor, etc.

Audio module 150 is used for converting digital audio information into analog audio signal to output, or for converting analog audio input into digital audio signal. Audio module 150 may also be used to encode and decode audio signals. In some embodiments, the audio module 150 may be disposed in the processor 110, or some functional modules of the audio module 150 may be disposed in the processor 110. In some embodiments, the audio module 150 may include a speaker, earpiece, microphone and headphone interface. For example, microphones can be used to provide multiple channels for acquiring calibration data or acquiring measurement signals.

In some embodiments, the mobile phone 10 further comprises a button 101, a motor and an indicator. The button 101 may include volume keys, on/off keys, etc.

Various embodiments of the mechanism disclosed in the present application may be implemented in hardware, software, firmware or a combination of these embodiments. Embodiments of the present application may be implemented as computer programs or program code executed on a programmable system comprising at least one processor, storage system (including volatile and non-volatile memory and/or memory elements), at least one input device, and at least one output device.

Program code may be applied to input instructions to perform the functions described in the present application and generate output information. Output information can be applied to one or more output devices in a known way. For the purposes of the present application, the processing system includes any system having a processor such as a digital signal processor (DSP), a microcontroller, a dedicated integrated circuit (ASIC) or a microprocessor or the like.

Program code can be implemented in a high-level procedural language or an object-oriented programming language, so as to communicate with the processing system. Program code can also be implemented in assembly language or machine language when needed. In fact, the mechanism described in the present application is not limited to the scope of any particular programming language. In either case, the language can be a compiler language or an interpretive language.

In some cases, the disclosed embodiments may be implemented in hardware, firmware, software, or any combination thereof. The disclosed embodiments may also be implemented as instructions carried by or stored on one or more temporary or non-transient machine-readable (e.g., computer-readable) storage media, which may be read and executed by one or more processors. For example, instructions can be distributed over a network or through other computer-readable media. Thus, machine-readable media may include any mechanism for storing or transmitting information in a machine-readable form (e.g., a computer), including, but not limited to, floppy disks, optical discs, optical disks, read-only memories (CD-ROMs), magnetic discs, read-only memories (ROMs), random access memory (RAM), erasable programmable read-only memory (EPROM), electrically erasable programmable read-only memory (EEPROM), magnetic or optical cards, flash memory, or tangible machine-readable memory utilizing the Internet with electrical, optical, acoustic or other forms of propagated signals to transmit information (e.g., carrier, infrared signal, digital signal, and the like). Thus, machine-readable media include any type of machine-readable medium suitable for storing or transmitting electronic instructions or information in a machine-readable form (e.g., a computer).

In the drawings, some structural or methodological features may be shown in a particular arrangement and/or sequence. However, it should be understood that such a specific arrangement and/or sequencing may not be required. Rather, in some embodiments, these features may be arranged in a manner and/or order different from those shown in the illustrative drawings. Further, the inclusion of structural or methodological features in a particular figure does not imply that such features are required in all embodiments, and in some embodiments, these features may not be included or may be combined with other features.

It should be noted that each unit/module mentioned in each device embodiment of the present application is a logical unit/module. Physically, a logical unit/module may be a physical unit/module, may also be part of a physical unit/module, can also be implemented in a combination of multiple physical units/modules. The physical implementation of these logical units/modules themselves is not the most important, and the combination of functions implemented by these logical units/modules is the key to solving the technical problems raised in the present application. Further, in order to highlight the innovative part of the present application, the above-mentioned device embodiments of the present application are not introduced into a unit/module that is not very closely related to solving the technical problems raised in the present application, which does not indicate that the above device embodiments do not have other units/modules.

It should be noted that in the examples and specifications of the present patent, relational terms such as first and second are only used to distinguish an entity or operation from another entity or operation, and do not necessarily require or imply any such actual relationship or order between these entities or operations. Further, the term "comprise", "comprising" or any other variation thereof is intended to cover non-exclusive inclusions so that a process, method, article or device comprising a series of elements includes not only those elements, but also other elements not expressly listed, or also includes elements inherent in such process, method, article or device. Without further restrictions, the element qualified by the statement "including one" does not exclude the existence of another identical element in the process, method, article or device comprising the element.

Although by reference to certain preferred embodiments of the present application, the present application has been illustrated and described, but those skilled in the art should understand that various changes may be made in form and details, without deviating from the spirit and scope of the present application.

What is claimed is:

1. A non-transitory computer-readable storage medium, wherein instructions are stored on the non-transitory computer-readable storage medium to make a computer perform an interference cancellation method, the interference cancellation method applied to an electronic device including first-type and second-type channels having signal reception function, comprising:

collecting, from the first-type channels, a measurement signal in which an effective signal and a first interference signal are mixed, and collecting a second interference signal from the second-type channels;

estimating the first interference signal in the measurement signal according to a coupling relationship between a first calibration data and a second calibration data and based on the second interference signal; and removing the first interference signal from the measurement signal to obtain a target effective signal;

wherein the first calibration data and the second calibration data are interference signals collected from the first-type channels and the second-type channels respectively when the electronic device is in a preset state, wherein the method further comprises obtaining a coefficient $C_{i,j}$ according to a formula $$S_{r,t}=\sum_{j=t-K}^{t+K}\sum_{i=1}^{M}C_{i,j}S_{i,j}$$

and the first calibration data and the second calibration data, wherein the coefficient $C_{i,j}$ is used to express the coupling relationship, and the coefficient $C_{i,j}$ is a time-invariant convolution kernel coefficient, and wherein a size of the convolution kernel is 2K+1, K is a natural number, $S_{r,j}$ is the t-th sampling data of the r-th first-type channel in the first calibration data, $S_{i,j}$ is the j-th sampling data of the i-th second-type channel in the second calibration data, the electronic device includes M second-type channels and N first-type channels, i takes a positive integer with a value of 1 to M, and r takes a positive integer with a value of 1 to N.

2. The method storage according to claim 1, wherein the coupling relationship is configured to express a frequency domain correlation between the interference signals in the first-type channels and the second-type channels, and the coupling relationship is continuous and smooth in the frequency domain.

3. The storage medium according to claim 1, wherein obtaining the coefficient $c_{i,j}$ according to the formula $$s_{r,t}=\sum\nolimits_{j=t-K}^{t+K}\sum\nolimits_{i=1}^{M}c_{i,j}s_{i,j}$$

and the first calibration data and the second calibration data comprising:

according to the formula $$s_{r,t}=\sum\nolimits_{j=t-K}^{t+K}\sum\nolimits_{i=1}^{M}c_{i,j}s_{i,j},$$

for each sampling data of the r-according to the formula th first-type channel in the first calibration data, obtaining an equation with the convolution kernel coefficient unknown, respectively, and obtaining a system of linear equations by combining all the equations, and obtaining the coefficient $c_{i,j}$ by solving the system of linear equations.

4. The storage medium according to claim 3, wherein estimating the first interference signal in the measurement signal according to the coupling relationship between the first calibration data and the second calibration data and based on the second interference signal, comprising:

estimating the second interference signal according to a formula $$s'_{r,t}=\sum\nolimits_{j=t-K}^{t+K}\sum\nolimits_{i=1}^{M}c_{i,j}s'_{i,j}$$

and the coefficient $c_{i,j}$ and the first interference signal, wherein $s'_{r,t}$ is the t-th sampling data of the r-th first-type channel in the second interference signal, and $s'_{i,j}$ is the j-th sampling data of the i-th second-type channel in the first interference signal.

5. The storage medium according to claim 1, wherein the electronic device is a magnetic resonance imaging device, the effective signal is a magnetic resonance imaging signal, the interference signal includes at least one of an electromagnetic interference signal and thermal noise;

the first-type channels are implemented by one or more phased array coils; the second-type channels are implemented by one or more phased array coils, or by one or more electrodes attached to a surface of a detection object.

6. The storage medium according to claim 1, wherein the electronic device is a synchronous EEG-functional magnetic resonance imaging device, the effective signal is an EEG signal, the interference signal includes at least one of a radio frequency signal and gradient signal generated by a magnetic resonance imaging device;

the first-type channels are implemented by one or more electrodes attached to a surface of a detection object; the second-type channels are implemented by one or more electrodes attached to the surface of the detection object, or by one or more phased array coils.

7. The storage medium according to claim 1, wherein the electronic device is a magnetic resonance imaging device comprising a transmitting coil, and the preset state is to close the transmitting coil;

the method further comprises:

in the case of the preset state, a signal collected from the first-type channels acts as the first calibration data, and a signal collected from the second-type channels acts as the second calibration data;

wherein a radio frequency signal transmitted by the transmitting coil is used to excite the first-type channels to receive the effective signal.

8. The storage medium according to claim 1, wherein the preset state is that the signal in the first-type channels and the second-type channels is collected multiple times;

the method further comprises:

in the case of the preset state, a first signal acts as the first calibration data, a second signal acts as the second calibration data;

wherein the first signal is a difference between two signals collected successively from the first-type channels, and the second signal is a difference between two signals collected successively from the second-type channels in the first interference signal.

9. The storage medium according to claim 1, wherein the electronic device is a magnetic resonance imaging device comprising a gradient coil, and the preset state is in a dead time during the collection of the measurement signal and the second interference signal;

in the case of the preset state, using a crusher gradient to damage effective signal from the gradient coil, to make a signal collected from the first-type channels act as the first calibration data, and make a signal collected from the second-type channels act as the second calibration data;

wherein the dead time is an interval time used to wait for a lateral or longitudinal magnetization vector until it returns to its original state when the magnetic resonance imaging device performs magnetic resonance imaging.

10. The method storage medium according to claim 1, wherein the electronic device is a magnetic resonance imaging device comprising a transmitting coil, and the preset state is that a high-frequency part in the frequency domain space in signals collected from the first-type channels and the second-type channels is dominated by electromagnetic interference; and wherein the high-frequency part in the frequency domain space of the measurement signal acts as the first calibration data, and the high-frequency part of in the frequency domain space of the second interference signal acts as the second calibration data.

11. The storage medium according to claim 1, wherein the measurement signal is one-dimensional or multidimensional data, and the convolution kernel is a one-dimensional or multidimensional convolution kernel.

12. An electronic device, comprising: one or more processors; one or more storage mediums according to claim 1.

* * * * *